US006241673B1

(12) United States Patent
Williams

(10) Patent No.: US 6,241,673 B1
(45) Date of Patent: Jun. 5, 2001

(54) DIAGNOSTIC MEDICAL ULTRASOUND SYSTEM WITH WIRELESS COMMUNICATION DEVICE

(75) Inventor: John A. Williams, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/237,548

(22) Filed: Jan. 26, 1999

(51) Int. Cl.$^7$ ........................................ A61B 8/00
(52) U.S. Cl. ............................. 600/437; 128/903
(58) Field of Search .................... 600/437, 407; 128/904, 903; 382/128, 130, 131, 132; 341/65; 705/3; 395/705

(56) References Cited

U.S. PATENT DOCUMENTS

| | | |
|---|---|---|
| 3,972,320 | 8/1976 | Kalman . |
| 4,100,916 | 7/1978 | King . |
| 4,413,629 | 11/1983 | Durley, III . |
| 4,522,213 | 6/1985 | Wallroth et al. . |
| 4,974,607 | 12/1990 | Miwa . |
| 5,291,399 | 3/1994 | Chaco . |
| 5,603,323 | 2/1997 | Pflugrath et al. . |
| 5,640,960 | 6/1997 | Jones et al. . |
| 5,715,823 | 2/1998 | Wood et al. . |
| 5,778,177 | * 7/1998 | Azar ................................. 395/200.32 |
| 5,851,186 | 12/1998 | Wood et al. . |
| 5,867,821 | * 2/1999 | Ballantyne et al. ..................... 705/2 |
| 5,891,035 | 4/1999 | Wood et al. . |
| 5,944,659 | * 8/1999 | Flach et al. .......................... 600/300 |
| 5,964,709 | * 10/1999 | Chiang et al. ....................... 600/447 |

* cited by examiner

Primary Examiner—Marvin M. Lateef
Assistant Examiner—Ali M. Imam
(74) Attorney, Agent, or Firm—Brinks Hofer Gilson & Lione

(57) ABSTRACT

A diagnostic medical ultrasound system with wireless communication device is provided. With these preferred embodiments, an ultrasound system can be made more portable by offloading ultrasound peripherals into a host network without the disadvantages concomitant with a wire connection to a network or modem jack. By using a wireless connection, the location of the ultrasound system is not limited to areas near a network jack, thereby increasing portability. The wireless connection also avoids the inconvenience of interrupting an ultrasound examination to plug the ultrasound system into the network jack. Further, by eliminating wire connections to a network jack, injury caused by an electrical short from a network line is also eliminated. Lastly, wireless communication between the ultrasound imaging system and the host network eliminates the need to retrofit old or existing buildings with cabling to connect the ultrasound imaging system with the host network.

33 Claims, 3 Drawing Sheets

DIAGNOSTIC MEDICAL ULTRASOUND SYSTEM WITH WIRELESS COMMUNICATION DEVICE

BACKGROUND

Many diagnostic medical ultrasound imaging systems are carried on a cart that has room for several on-cart peripherals. For example, an ultrasound cart often carries a printer or video-tape recorder for generating a hard copy of an ultrasound image. The convenience of having on-cart access to peripherals comes at the price of adding weight to the ultrasound cart, thereby making the ultrasound system less portable. To increase portability, some or all of the peripherals can be moved off the ultrasound cart and placed into a host network, which can also provide the ultrasound system with access to equipment not commonly found on the cart. To provide access to network-based peripherals, an ultrasound system typically has a wire connection, such as an RS-232 or 10baseT Ethernet connection, to a network or modem wall jack. In operation, if a user wishes to move the ultrasound system to another location, he unplugs the wire connection from the network jack, wheels the ultrasound system cart to the new location, and plugs the wire connection into the network jack of the new location.

There are several disadvantages associated with this implementation. First, in order to support the network connection, the network wall outlet must be near the ultrasound work area. This limits the portability of the ultrasound system. Second, users sometimes begin an ultrasound examination before remembering to plug the wire connection into the network jack of the new location. These users may need to interrupt an examination in progress to make the network connection. Third, this implementation presents several safety concerns. For example, if there is an electrical short from a network line to a high-voltage source (power lines, power transformers, lightening, etc.), the patient can be injured, especially during an intra-cavity ultrasound examination.

There is, therefore, a need for an improved diagnostic medical ultrasound system to overcome the problems described above.

SUMMARY

The present invention is defined by the following claims, and nothing in this section should be taken as a limitation on those claims.

By way of introduction, the preferred embodiments described below include a diagnostic medical ultrasound system with a wireless communication device. With these preferred embodiments, an ultrasound system can be made more portable by offloading ultrasound peripherals into a host network without the disadvantages concomitant with a wire connection to a network or modem jack. By using a wireless connection, the location of the ultrasound system is not limited to areas near a network jack, thereby increasing portability. The wireless connection also avoids the inconvenience of interrupting an ultrasound examination to plug the ultrasound system into the network jack. Further, by eliminating wire connections to a network jack, injury caused by an electrical short from a network line is also eliminated. Lastly, wireless communication between the ultrasound imaging system and the host network eliminates the need to retrofit old or existing buildings with cabling to connect the ultrasound imaging system with the host network.

The preferred embodiments will now be described with reference to the attached drawings.

DETAILED DESCRIPTION OF THE PRESENTLY PREFERRED EMBODIMENTS

Figure 1:
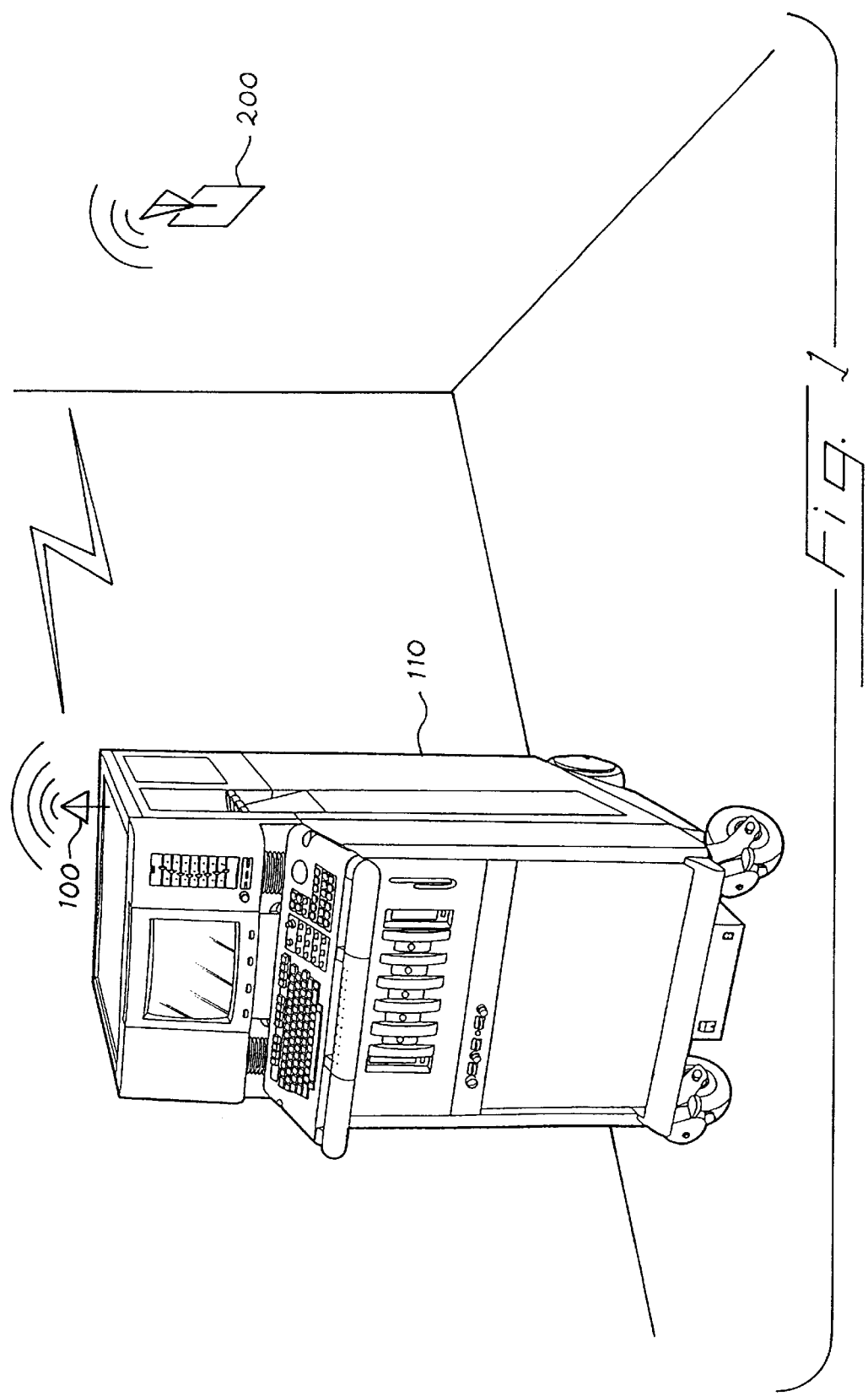
FIG. 1 is an illustration of a presently preferred diagnostic medical ultrasound system having a wireless communication device.

Turning now to the drawings, FIG. 1 is an illustration of a diagnostic medical ultrasound system 110 of a presently preferred embodiment. The ultrasound imaging system 110 has a wireless communication device 100 that is operative to establish a wireless communication connection with a second wireless communication device 200. In the embodiment shown in FIG. 1, the second wireless communication device 200 is located in the same room as the ultrasound system 110, although the second wireless communication device 200 can be located in another location. As used herein, the term "wireless communication device" refers to any device that has the ability to transport analog or digital data from one point to another without the use of a physical connection, such as by using radio frequency, light wave, or microwave transmission. One suitable wireless communication device is available from OTC Telecom under the trade name AIREZY.

The first and second wireless communication devices 100, 200 are used to wirelessly transmit ultrasound data between the ultrasound system 110 and an ultrasound peripheral coupled with the second wireless communication device 200. As used herein, the term "coupled with" means directly coupled with or indirectly coupled with through one or more components. For simplicity, the term "ultrasound data" is used in the specification and claims to broadly refer to any data that can be processed by the ultrasound system's processor. Ultrasound data includes, but is not limited to, ultrasound examination data, images, audio data, calculations, reports, screen captures of measurements or report data, indications of diagnosis, raw system data (such as prescan-converted acoustic data, physio waveforms, operating parameters, and front-end complex data of coherent beam forming systems), information about the ultrasound system, information about an ultrasound peripheral, and software applications that can be installed by the ultrasound system's processor.

Also for simplicity, the term "ultrasound peripheral" is used in the specification and claims to broadly refer to any device that can receive ultrasound data from the ultrasound system 110 and/or that can transmit ultrasound data to the ultrasound system 110. The widest variety of devices can be used as ultrasound peripherals, such as, but not limited to, video imagers, digital workstations, analog or digital mass storage devices, analog or digital video recording devices, printers, as well as other ultrasound imaging systems. In some situations, a device, such as a printer, can be used in the network to receive both ultrasound data (hence, acting as an ultrasound peripheral) and non-ultrasound data from other devices or applications.

Figure 2:
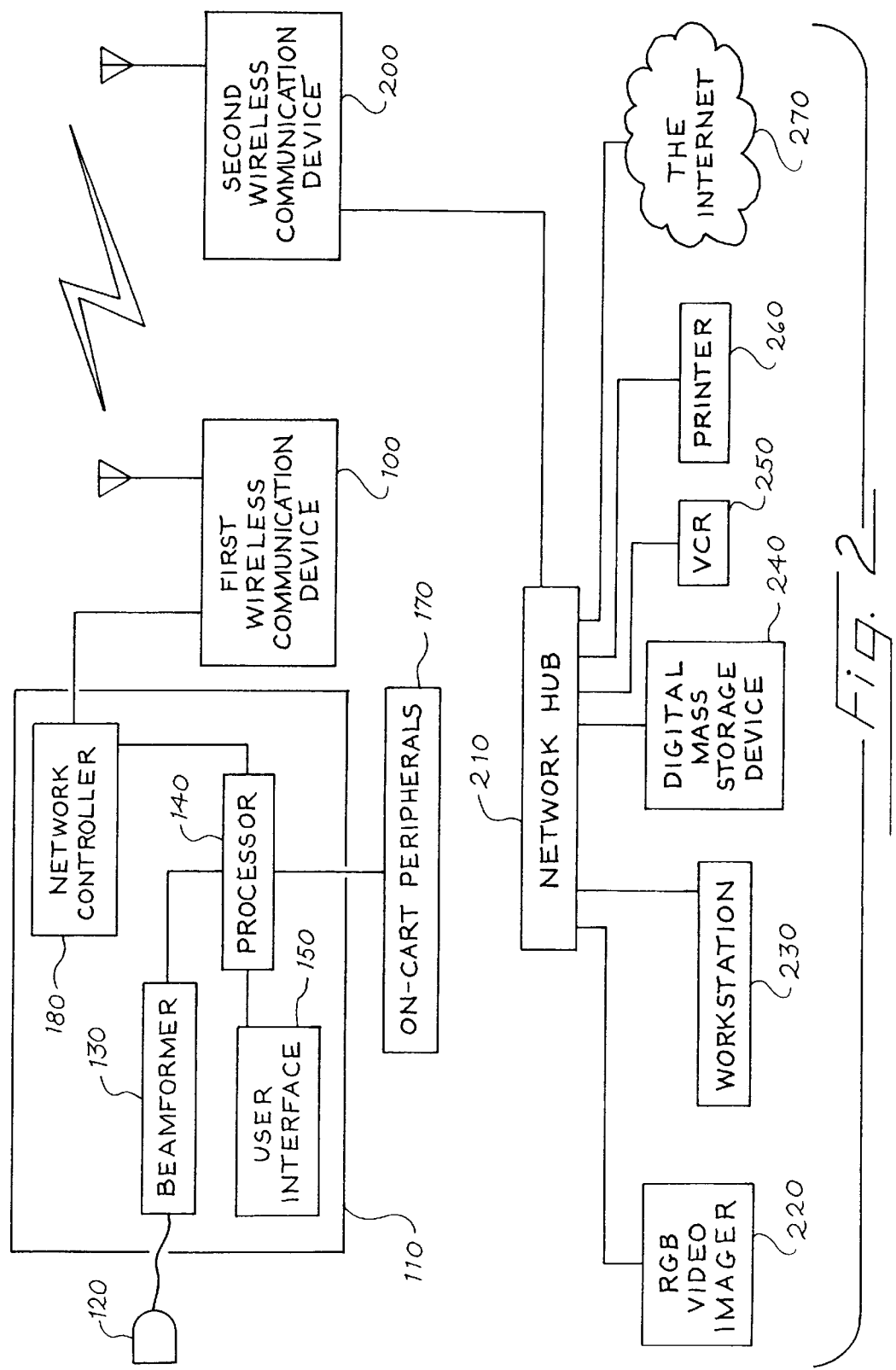
FIG. 2 is a block diagram of a preferred diagnostic medical ultrasound system and host network.

Turning again to the drawings, FIG. 2 is a block diagram showing a preferred implementation of the ultrasound system 110, as well as a preferred implementation of a network in wireless communication with the ultrasound system 110.

As shown in FIG. 2, the ultrasound system 110 comprises a transducer 120 coupled with a beamformer 130 for transmitting ultrasonic energy into and receiving echo signals from tissue. An electrical representation of the returned echo signals is sent from the beamformer 130 to the processor 140. The processor 140 also responds to information and commands entered through the user interface 150 and controls the operation of the ultrasound system 110.

To transmit ultrasound data to an on-cart peripheral 170 connected to the ultrasound system 110 with a wired connection, the processor provides the ultrasound data directly to the on-cart peripheral 170, such as a display monitor. To transmit ultrasound data to an ultrasound peripheral that is not wired to the ultrasound system 110, the processor 140 provides a network controller 180 with an instruction to transmit ultrasound data as well as with the location of the ultrasound data to be transmitted. The network controller 180 retrieves the ultrasound data from the location and then packages and addresses the data according to a network protocol such as IEEE 802, TCP/IP, or UDP, for example. The network controller 180 then delivers the ultrasound data to the first wireless communication device 100 for wireless transmission to an ultrasound peripheral. A preferred method for transmitting ultrasound data to an ultrasound peripheral is shown in the flow chart of FIG. 3.

Figure 3:
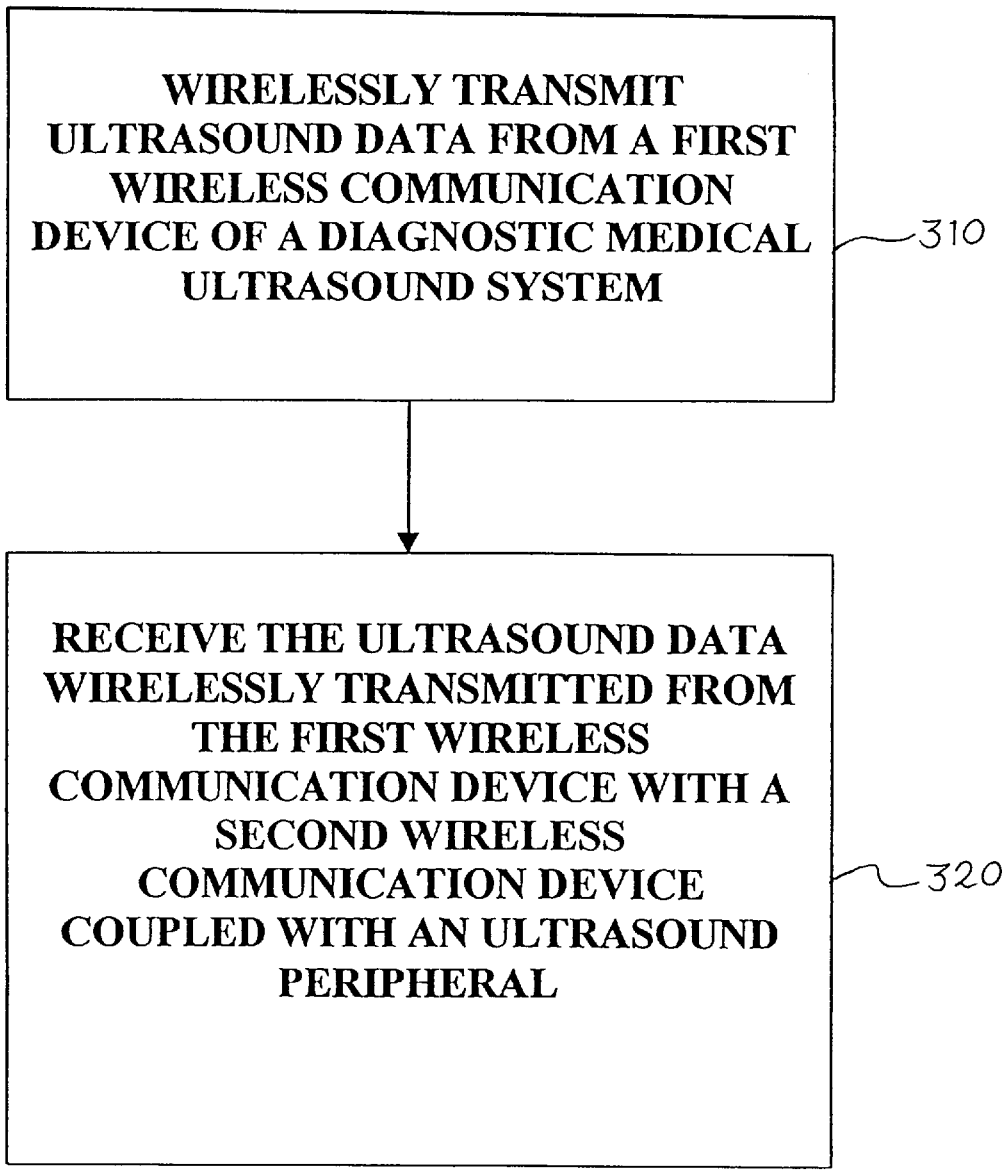
FIG. 3 is a flow chart of a preferred method for transmitting ultrasound data between a diagnostic medical ultrasound system and an ultrasound peripheral.

As shown in FIG. 3, this method first comprises the step of wirelessly transmitting ultrasound data from the first wireless communication device of the diagnostic medical ultrasound system (step 310). In operation, the first wireless communication device 100 encodes the ultrasound data to modulate a wireless transmitter, such as a radio frequency, light wave, or microwave transmitter. Several modulation and encoding techniques can be used, such as amplitude modulation, frequency modulation, or phase modulation. Variants or combination of these techniques can also be used. One of the most popular modulations techniques is known as spread spectrum.

Next, the second wireless communication device 200 receives the ultrasound data wirelessly transmitted by the first wireless communication device 100 (step 320). After the second wireless communication device 200 detects, demodulates, and decodes the ultrasound data, the ultrasound data is delivered to a network hub 210 coupled with the second wireless communication device 200. In the preferred embodiment illustrated in FIG. 2, the network hub 210 is coupled with a variety of ultrasound peripherals—an RGB video imager 220, a digital ultrasound workstation 230, a digital mass storage device 240, a video recording device 250, and a printer 260. The network hub 210 is also indirectly coupled with ultrasound peripherals located in the Internet 270. Although not shown, the network hub 210 can be wired or wirelessly coupled with one or more additional ultrasound systems. In this way, each ultrasound system can benefit from the shared ultrasound peripherals on the network. When ultrasound data is sent to the network hub 210 from the second wireless communication device 200, the network hub 210 directs the ultrasound data to the intended ultrasound peripheral according to network protocol.

In addition to transmitting ultrasound data, the ultrasound imaging system 110 can receive ultrasound data with the first wireless communication device 100. For example, the ultrasound imaging system 110 can request a specific ultrasound image stored in the digital mass storage device 240. The ultrasound imaging system 110 can send the request for the image to the digital mass storage device 240 as described above. In response to this request, a network controller in the digital mass storage device 240 formats and addresses the image for delivery to the ultrasound imaging system 110 and transfers the image to the network hub 210, which wirelessly transmits the image to the ultrasound imaging system 110 via the first and second wireless communication devices 100, 200.

There are several advantages associated with these preferred embodiments. With these preferred embodiments, an ultrasound system can be made more portable by offloading ultrasound peripherals into a host network without the disadvantages concomitant with a wire connection to a network or modem jack. By using a wireless connection, the location of the ultrasound system is no longer limited to areas near a network jack, thereby increasing portability. The wireless connection also avoids the inconvenience of interrupting an ultrasound examination to plug the ultrasound system into the network jack. Further, by eliminating wire connections to a network jack, injury caused by an electrical short from a network line is also eliminated. Lastly, wireless communication between the ultrasound imaging system and the host network eliminates the need to retrofit old or existing buildings with cabling to connect the ultrasound imaging system with the host network.

There are several alternatives to the preferred embodiments described above. For example, the first wireless communication device 100 can be an original component of the ultrasound imaging system 110 or can be added as an accessory to an existing ultrasound imaging system. For example, the first wireless communication device 100 can be plugged into an Ethernet port found on some ultrasound imaging systems. Additionally, while the preferred embodiment illustrated in FIG. 2 shows multiple ultrasound peripherals coupled with a single wireless communication device via a network hub, a single ultrasound peripheral can be coupled with the network hub. In another alternate embodiment, the network hub is not used, and a single wireless communication device is coupled with a single ultrasound peripheral. For example, the second wireless communication device can be dedicated to a single printer.

Further, the functionality associated with one or more of the described components can be combined or distributed to other components. For example, the processor 140 can perform some or all of the functions associated above with the network controller 180. Additionally, some of the components described above may not be needed in all embodiments. Lastly, the widest variety of network media (link layers) can be used, including Ethernet (10baseT, 100baseT, Gigabit, Thick, Thin), Token Ring, FDDDI, SLIP, PPP, Asynchronous Transfer Mode (ATM), IEEE 1394 (Firewire), RS-232 Serial, RS-422 Serial, Universal Serial Bus (USB), and Appletalk.

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

What is claimed is:

1. A diagnostic medical ultrasound system comprising:
   a first wireless communication device operative to wirelessly communicate with a second wireless communication device coupled with an ultrasound peripheral; and
   a processor coupled with the first wireless communication device and operative to transmit ultrasound data to the ultrasound peripheral via the first wireless communication device.

2. The diagnostic medical ultrasound system of claim 1, wherein the processor is further operative to receive ultrasound data from the ultrasound peripheral via the first wireless communication device.

3. The diagnostic medical ultrasound system of claim 1 further comprising a network controller coupled with the processor and the first wireless communication device and operative to control transmission of ultrasound data to the ultrasound peripheral.

4. The diagnostic medical ultrasound system of claim 3, wherein the network controller comprises an Ethernet controller.

5. The diagnostic medical ultrasound system of claim 1, wherein the second wireless communication device is coupled with a plurality of ultrasound peripherals through a network hub.

6. The diagnostic medical ultrasound system of claim 5, wherein the plurality of ultrasound peripherals are shared with at least one other diagnostic medical ultrasound system.

7. A diagnostic medical ultrasound imaging network comprising:
- an ultrasound imaging system comprising a first wireless communication device;
- a second wireless communication device in wireless communication with the ultrasound imaging system via the first wireless communication device; and
- an ultrasound peripheral coupled with the second wireless communication device;
- the ultrasound imaging system operative to transmit ultrasound data to the ultrasound peripheral via the first and second wireless communication devices.

8. The diagnostic medical ultrasound imaging network of claim 7, wherein the ultrasound imaging system is further operative to receive ultrasound data from the ultrasound peripheral via the first and second wireless communication devices.

9. The diagnostic medical ultrasound imaging network of claim 7, wherein the ultrasound peripheral comprises an RGB video imager.

10. The diagnostic medical ultrasound imaging network of claim 7, wherein the ultrasound peripheral comprises a digital ultrasound workstation.

11. The diagnostic medical ultrasound imaging network of claim 7, wherein the ultrasound peripheral comprises a digital mass storage device.

12. The diagnostic medical ultrasound imaging network of claim 7, wherein the ultrasound peripheral comprises a video recording device.

13. The diagnostic medical ultrasound imaging network of claim 7, wherein the ultrasound peripheral comprises a printer.

14. The diagnostic medical ultrasound imaging network of claim 7, wherein the ultrasound peripheral is coupled with the second wireless communication device via the Internet.

15. The diagnostic medical ultrasound imaging network of claim 7 further comprising a network hub, and wherein the ultrasound peripheral is coupled with the second wireless communication device via a network hub.

16. The diagnostic medical ultrasound imaging network of claim 15 further comprising at least one additional ultrasound peripheral coupled with the network hub.

17. The diagnostic medical ultrasound imaging network of claim 15, wherein the network hub comprises an Ethernet hub.

18. The diagnostic medical ultrasound imaging network of claim 15 further comprising at least one other diagnostic medical ultrasound system coupled with the network hub.

19. A method for transmitting ultrasound data between a diagnostic medical ultrasound system and an ultrasound peripheral, the method comprising:

(a) wirelessly transmitting ultrasound data from a first wireless communication device of a diagnostic medical ultrasound system; and (b) receiving the ultrasound data wirelessly transmitted in (a) with a second wireless communication device coupled with an ultrasound peripheral.

20. The method of claim 19 further comprising:

(c) wirelessly transmitting ultrasound data from the ultrasound peripheral via the second wireless communication device; and (d) receiving, with the first wireless communication device, the ultrasound data wirelessly transmitted in (c).

21. The method of claim 19, wherein (b) comprises receiving the ultrasound data wirelessly transmitted in (a) with a second wireless communication device coupled with a RGB video imager.

22. The method of claim 19, wherein (b) comprises receiving the ultrasound data wirelessly transmitted in (a) with a second wireless communication device coupled with a digital ultrasound workstation.

23. The method of claim 19, wherein (b) comprises receiving the ultrasound data wirelessly transmitted in (a) with a second wireless communication device coupled with a digital mass storage device.

24. The method of claim 19, wherein (b) comprises receiving the ultrasound data wirelessly transmitted in (a) with a second wireless communication device coupled with a video recording device.

25. The method of claim 19, wherein (b) comprises receiving the ultrasound data wirelessly transmitted in (a) with a second wireless communication device coupled with a printer.

26. The method of claim 19, wherein (b) comprises receiving the ultrasound data wirelessly transmitted in (a) with a second wireless communication device coupled with an ultrasound peripheral via the Internet.

27. The method of claim 19, wherein (b) comprises receiving the ultrasound data wirelessly transmitted in (a) with a second wireless communication device coupled with an ultrasound peripheral via a network hub.

28. A diagnostic medical ultrasound system comprising:
- an ultrasound system cart;
- a wireless communication device carried by the ultrasound system cart; and
- a processor carried by the ultrasound system cart and coupled with the wireless communication device, the processor operative to transmit ultrasound data via the wireless communication device to an ultrasound peripheral not carried by the ultrasound system cart.

29. The invention of claim 28, wherein the processor is further operative to receive ultrasound data via the wireless communication device from an ultrasound peripheral located external to the ultrasound system cart.

30. The invention of claim 28, wherein the wireless communication device is an original component of the ultrasound imaging system.

31. The invention of claim 28, wherein the wireless communication device is an accessory to an existing ultrasound imaging system.

32. The invention of claim 28, wherein the ultrasound peripheral is coupled with a second wireless communication device.

33. The invention of claim 28, wherein the ultrasound peripheral is coupled with a network hub and wherein the network hub is coupled with a second wireless communication device.

\* \* \* \* \*